United States Patent
Mark et al.

(10) Patent No.: US 10,456,061 B2
(45) Date of Patent: Oct. 29, 2019

(54) HOLDING ARRANGEMENT FOR A SURGICAL ACCESS SYSTEM

(71) Applicant: Nico Corporation, Indianapolis, IN (US)

(72) Inventors: Joseph L. Mark, Indianapolis, IN (US); Brian C. Dougherty, Terre Haute, IN (US)

(73) Assignee: Nico Corporation, Indianapolis, IN (US)

( * ) Notice: Subject to any disclaimer, the term of this patent is extended or adjusted under 35 U.S.C. 154(b) by 1048 days.

(21) Appl. No.: 14/885,417

(22) Filed: Oct. 16, 2015

(65) Prior Publication Data

US 2016/0128720 A1    May 12, 2016

Related U.S. Application Data

(60) Provisional application No. 62/078,575, filed on Nov. 12, 2014.

(51) Int. Cl.
*A61B 17/34* (2006.01)
*A61B 5/055* (2006.01)
(Continued)

(52) U.S. Cl.
CPC .......... *A61B 5/055* (2013.01); *A61B 17/3421* (2013.01); *A61B 50/20* (2016.02);
(Continued)

(58) Field of Classification Search
CPC .................... A61B 50/20; A61B 5/055; A61B 2017/00911; A61B 2019/208;
(Continued)

(56) References Cited

U.S. PATENT DOCUMENTS 3,690,323 A    9/1972   Wortman et al.
4,165,745 A *  8/1979   Heifetz .............. A61B 17/2804
                                            294/99.2
(Continued)

FOREIGN PATENT DOCUMENTS

RU   2009124446 A   1/2011
WO   2006017507 A2  2/2006
(Continued)

OTHER PUBLICATIONS

PCT International Search Report dated Jul. 24, 2014 for PCT/US2014/015755.

(Continued)

*Primary Examiner* — Navin Natnithithadha
*Assistant Examiner* — Sunita Reddy
(74) *Attorney, Agent, or Firm* — Kristin L. Murphy; Honigman LLP

(57) ABSTRACT

A holding arrangement for a surgical access assembly is disclosed. One holding arrangement includes a holder member and a support member configured to engage with the holder member. The support member supports an outer sheath of a surgical assembly. The support member is compatible with a magnetic resonance imaging device. Another holding arrangement includes a holder member configured to hold a medical or diagnostic device such as a catheter.

12 Claims, 5 Drawing Sheets

(51) Int. Cl.
*A61B 17/02* (2006.01)
*A61B 50/20* (2016.01)
*A61B 90/50* (2016.01)
A61B 17/00 (2006.01)
A61B 90/10 (2016.01)
A61B 90/11 (2016.01)

(52) U.S. Cl.
CPC .............. *A61B 90/50* (2016.02); *A61B 90/11* (2016.02); *A61B 2017/00911* (2013.01); *A61B 2017/3407* (2013.01); *A61B 2017/3492* (2013.01); *A61B 2090/103* (2016.02)

(58) Field of Classification Search
CPC ........ A61B 17/3421; A61B 2017/3407; A61B 90/50; A61B 90/11; A61B 2017/3492
USPC .................................. 600/417, 204; 128/897
See application file for complete search history.

(56) References Cited

U.S. PATENT DOCUMENTS

| | | | |
|---|---|---|---|
| 4,386,602 A | 6/1983 | Sheldon et al. | |
| 4,638,798 A | 1/1987 | Shelden et al. | |
| 5,183,464 A | 2/1993 | Dubrui et al. | |
| 5,217,441 A | 6/1993 | Shichman | |
| 5,320,611 A | 6/1994 | Bonutti et al. | |
| 5,431,676 A | 7/1995 | Dubrul et al. | |
| 5,441,042 A * | 8/1995 | Putman | B25J 9/042 600/102 |
| 5,860,996 A | 1/1999 | Urban et al. | |
| 5,876,410 A * | 3/1999 | Petillo | A61B 17/128 606/139 |
| 5,904,702 A * | 5/1999 | Ek | A61B 17/29 606/206 |
| 6,047,218 A | 4/2000 | Whayne et al. | |
| 6,129,685 A | 10/2000 | Howard, III | |
| 6,179,826 B1 | 1/2001 | Aebischer et al. | |
| 6,226,548 B1 | 5/2001 | Foley et al. | |
| 6,245,052 B1 | 6/2001 | Orth et al. | |
| 6,280,399 B1 | 8/2001 | Rossin et al. | |
| 6,293,952 B1 | 9/2001 | Brosens et al. | |
| 6,331,180 B1 | 12/2001 | Cosman et al. | |
| 6,374,135 B1 | 4/2002 | Bucholz | |
| 6,416,520 B1 * | 7/2002 | Kynast | A61B 90/11 606/130 |
| 6,669,685 B1 | 12/2003 | Rizoiu et al. | |
| 6,942,634 B2 | 9/2005 | Odland | |
| 7,857,271 B2 | 12/2010 | Lees | |
| 8,979,735 B2 * | 3/2015 | Augarten | A61F 5/0059 108/137 |
| 2002/0038116 A1 * | 3/2002 | Lee | A61B 5/0084 606/1 |
| 2003/0073934 A1 | 4/2003 | Putz | |
| 2003/0191371 A1 | 10/2003 | Smith et al. | |
| 2004/0024291 A1 | 2/2004 | Zinkel | |
| 2004/0059375 A1 | 3/2004 | Ginn et al. | |
| 2004/0068172 A1 | 4/2004 | Nowinski et al. | |
| 2004/0077938 A1 * | 4/2004 | Mark | A61B 10/0275 600/411 |
| 2004/0102804 A1 | 5/2004 | Chin | |
| 2004/0149874 A1 * | 8/2004 | Stoianovici | F16M 11/12 248/276.1 |
| 2004/0152968 A1 * | 8/2004 | Iversen | A61B 17/00 600/411 |
| 2004/0186346 A1 | 9/2004 | Smith et al. | |
| 2004/0215143 A1 | 10/2004 | Brady et al. | |
| 2005/0148808 A1 * | 7/2005 | Cameron | A61G 15/125 600/13 |
| 2005/0193451 A1 * | 9/2005 | Quistgaard | A61B 5/6843 414/1 |
| 2006/0122496 A1 * | 6/2006 | George | A61B 5/055 600/424 |
| 2006/0161039 A1 * | 7/2006 | Juliana | A61N 2/006 600/9 |
| 2007/0100211 A1 | 5/2007 | Selover et al. | |
| 2007/0270898 A1 | 11/2007 | Lillehei | |
| 2009/0048622 A1 | 2/2009 | Wilson | |
| 2009/0312611 A1 | 12/2009 | Mangiardi | |
| 2010/0010315 A1 | 1/2010 | Mangiardi | |
| 2010/0122419 A1 * | 5/2010 | Zupancic-Albin | A61J 7/0007 7/125 |
| 2011/0152903 A1 * | 6/2011 | Wiedenbein | A61B 17/122 606/158 |
| 2012/0253353 A1 | 10/2012 | McBride | |
| 2012/0289816 A1 * | 11/2012 | Mark | A61M 39/0247 600/411 |
| 2013/0102851 A1 * | 4/2013 | Mark | A61B 17/3468 600/233 |
| 2013/0304216 A1 * | 11/2013 | Paspa | A61N 1/0539 623/17.19 |
| 2014/0107665 A1 * | 4/2014 | Shellenberger | A61B 34/30 606/130 |
| 2014/0133627 A1 * | 5/2014 | Sakuragi | A61B 6/4429 378/62 |
| 2014/0288578 A1 * | 9/2014 | Solar | A61B 17/00234 606/130 |
| 2015/0327765 A1 * | 11/2015 | Crane | A61B 5/0059 348/77 |
| 2018/0064364 A1 * | 3/2018 | Oziel | A61B 5/7214 |

FOREIGN PATENT DOCUMENTS

| | | |
|---|---|---|
| WO | 2006050047 A2 | 5/2006 |
| WO | 2007002251 A2 | 1/2007 |
| WO | 2008066543 A1 | 6/2008 |
| WO | 2008121294 A1 | 10/2008 |

OTHER PUBLICATIONS

PCT International Search Report and Opinion dated Apr. 9, 2013 for PCT/US2012/061568.
PCT International Search Report dated Jun. 20, 2006 for PCT/US05/39185.
Manuel Dujovny, et al., "Brain Retractor Systems," Neurological Research, vol. 37, No. 7, (2010).
O. Barlas, et al., Clincial Article, Stereotractically guided microsurgical removal of colloid cysts, Acta Neurochir (Wien) (2004).

* cited by examiner

HOLDING ARRANGEMENT FOR A SURGICAL ACCESS SYSTEM

TECHNICAL FIELD

The present disclosure relates generally to a holding arrangement for a surgical device for use with delicate and critical tissues; the holding arrangement being compatible with magnetic resonance imaging (MRI).

BACKGROUND

Magnetic Resonance Imaging (MRI) has a wide range of applications in medical diagnosis and has become the investigative tool of choice for neurological abnormalities due to its heightened sensitivity for small tumors and ability to offer higher quality tissue visualization. Moreover, MRI provides a sufficient contrast between variations of tissues within the white matter and the gray matter as well as to provide accurate differentiation of many conditions of the brain. However, since MRI forms a strong magnetic field around the area to be imaged, it is necessary for safety and imaging quality to ensure that materials that induce significant susceptibility can be used in the bore of the MRI or the immediate region of the bore.

Notwithstanding the foregoing advances in imaging technology and both frame and frameless stereotactic image guidance techniques, there remains a need for an improved surgical techniques and apparatus for diagnostic and intervention procedures for brain tissue, including mechanisms for holding a surgical access system in place that allows for effective access to the area of interest, can be secured to the patient, while improving accuracy, freeing a surgeon's hand for other procedural activities, and is compatible with imaging technology, especially MRI. Specifically, there is a need for a holding arrangement compatible with MRI to allow use of MRI for diagnostic and interventional capabilities while providing an effective non-distortional imaging environment while being safe for the patient and the clinical staff.

SUMMARY

An exemplary holder member of a holding arrangement for a surgical access assembly is disclosed. The holder comprises: one or more legs, each having a base and a pair of jaws. The one or more legs, one or more bases, and/or the pair of jaws maybe malleable.

Another exemplary holding arrangement for a surgical access assembly is disclosed. The holding arrangement comprises: a holder member and a support member selectively engageable with the holder member. At least the support member is compatible with a magnetic resonance imaging device.

BRIEF DESCRIPTION OF THE DRAWINGS

Exemplary embodiments of the present disclosure will now be described in greater detail with reference to the attached figures, in which.

DETAILED DESCRIPTION

Figure 1:
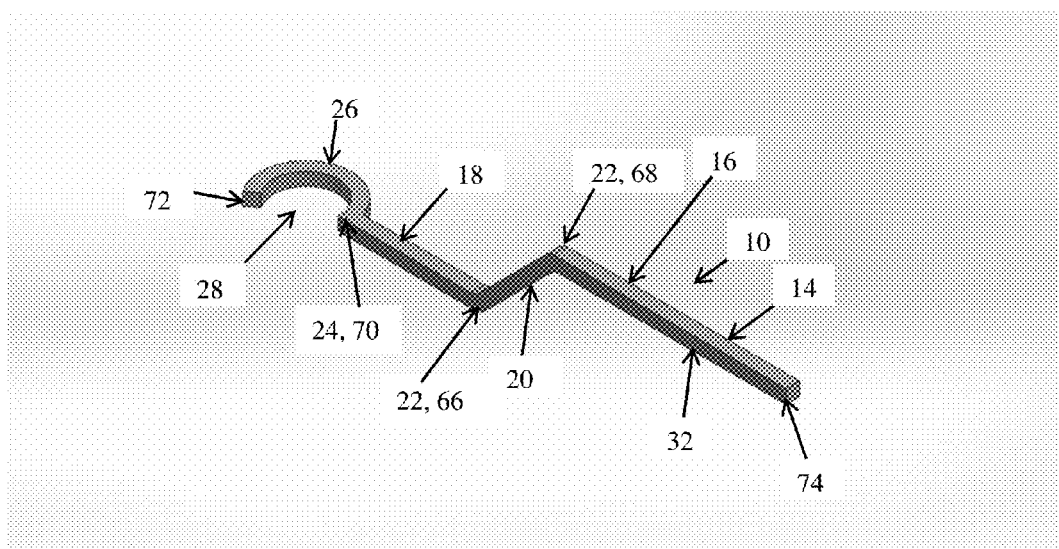
FIG. 1 is a perspective view of an example of a support member.

Referring now to the discussion that follows and also to the drawings, illustrative approaches to the disclosed assemblies and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is a holding arrangement for a surgical access system compatible with MRI technology, various components of the holding arrangement, and a method of using same. The components described herein provide surgeons with an enhanced ability to minimize trauma to the patient during intracranial diagnosis and surgical treatment.

More specifically, a holding arrangement for a surgical access system is disclosed. A surgical access system may be any intracranial surgical access system which may be supported by the holding arrangement in such a way that the surgical access system can perform its function. In one exemplary arrangement, the surgical system comprises one or more outer sheaths, one or more removable medical or diagnostic and/or surgical devices, at least some of which can be inserted in and out of the outer sheath of the holding arrangement. Such a device may be, for example, an obturator, a navigational stylet, a drainage catheter, a device for delivery of a therapeutic, a probe such as an ultrasound probe, more preferably an MRI probe, or another device to be utilized during intracranial diagnosis and/or a surgical procedure. In another non-limiting exemplary embodiment, the holding arrangement comprises a plurality of holder members and a plurality of support members and/or a plurality of medical or diagnostic devices.

Referring to FIG. 1, an exemplary arrangement of a support member 10 of a holding arrangement 12 (best seen in FIG. 4) is shown. The support member 10 may be integrally formed or comprise two or more separate elements, for example, the proximal section 16, the retaining section 18, the shaft section 20, and the retaining member 26, that are connected together. The support member 10 may have any length and thickness, depending on requirements of a specific application. In one exemplary arrangement, the support member 10 is a generally elongated piece. As best seen in FIG. 1, the support member 10 is shaped as a shaft. The support member 10 is flexible, rigid or a combination thereof. The body 14 of the support member 10 may have any cross section. For example, the cross section of the body 10 may be a square, a rectangle, an oval, a circle, a diamond, a triangle, a pentagon, a hexagon, an octagon, a trapezoid, the like, or a combination thereof. As is shown in FIG. 4, the cross section of the body 14 matches the cross section of the notch 52 of the holder member 36.

In one exemplary arrangement, the body 14 of the support member 10 comprises a plurality of sections: the engagement portion 32, the proximal section 16, the retaining section 18, and the shaft section 20. In one exemplary configuration, the body 14 of the support member 10 is configured in one plane. In another exemplary arrangement, as seen in FIG. 1, the proximal section 16 with the retaining member 26 are in a different plane than the retaining section 18. The proximal section 16 is connected to the retaining section 18 with the shaft section 20. The shaft section 20 is oriented at a 45° angle. The shaft section 20 may be disposed at 30° or more, 45° or more, 60° or more, 75° or more. In an alternative configuration, the shaft section 20 may be disposed at 220° or less, 150° or less, 120° or less, or 90° or less.

Figure 4:
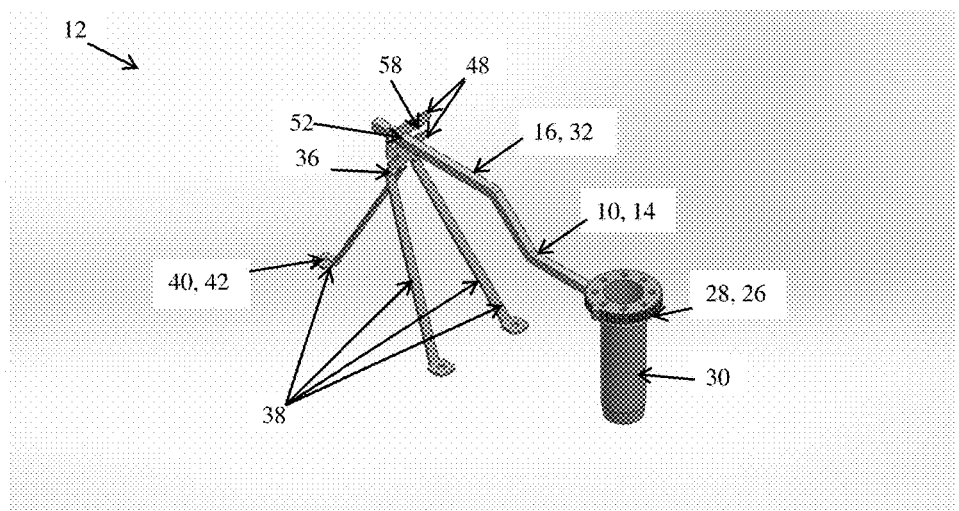
FIG. 4 illustrates an exemplary holding arrangement with the outer sheath of a surgical access system engaged with the support member.

In the exemplary arrangement shown in FIGS. 1 and 4, the support member 10 comprises two bend points 22, separated by the shaft section 20 of the body 14. The first bend point 66 is located proximal of the distal end 70 of the body 14. Together with the retaining end 24, the first bend 66 defines the retaining section 18. The second bend point 68 is positioned proximal of the shaft section 20 and together with the proximal end 74 defines the proximal section 16.

The proximal section 16 of the support member 10 engages the holder member 36 so that the support member 10 can be attached, secured, or both, to a patient's skull which secures the desired X-Y-Z position of the sheath and frees the surgeon's hands. The proximal section 16 may be attached and/or secured before, during, or after the outer sheath 30 is successfully positioned in tissue.

In one exemplary arrangement, the proximal section 16, the shaft section 20, and/or the retaining section 18, and/or one or more portions thereof, comprise the engagement portion 32 of the support member 10. As best seen in FIG. 4, the engagement portion 32 is inserted within the notch 52 of the holder member 36. In the exemplary arrangement depicted in FIG. 4, the proximal section 16 comprises the engagement portion 32. The entire length of the proximal section 16 may serve as the engagement portion 32 so that any portion of the proximal section 16 may engage the holder member 36.

As can be seen in FIG. 1, the retaining section 18 connects the shaft section 20 with the retaining member 26. The retaining member 26 is integrally formed with the retaining section 18. In an alternative arrangement, the retaining member 26 is formed separately and connected to the retaining section 18. The retaining member 26 engages, holds, and supports the body of the outer sheath 62 in such a way that the outer sheath 30 may be manipulated by the surgeon.

As shown in FIGS. 1 and 4, the retaining member 26 has a curved shape so that the retaining member 26 curves back towards the retaining end 24, defining an opening 28 between an end of a retaining member 72 and the retaining end 24 of the retaining section 18. The opening 28 may have any diameter so that the outer sheath 30 fits within the opening 28. The outer sheath 30 fits within the opening 28 in such a way that the outer sheath 30 is easy to insert within the opening 28, but the outer sheath 30 is not loose within the opening 28. In one exemplary arrangement, the retaining member 26 forms a half circle. In alternative arrangements, the retaining member 26 may form a full circle, less than a full circle, or a less than a half circle. The retaining member 26 may be flexible or inflexible. In one exemplary configuration, the retaining member 26 may function as a spring clip so that the retaining member 26 snaps partially around the outer sheath 30.

Figure 2:
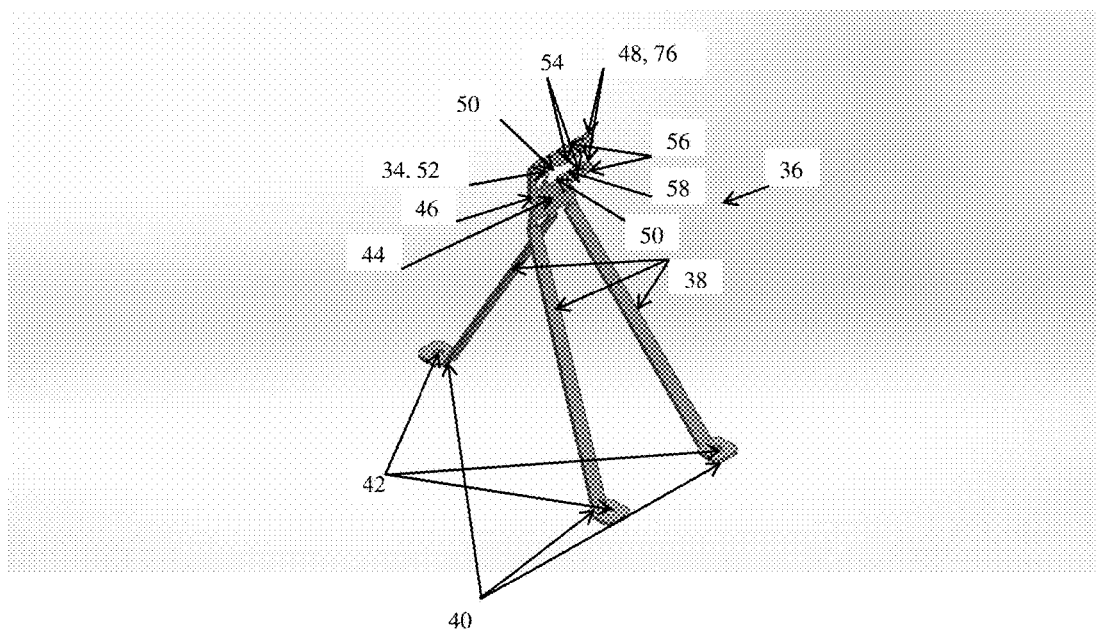
FIG. 2 is a perspective view of a holder member.

FIG. 2 illustrates an example of a holder member 36. The holder member 36 is free standing and/or attachable to patient's skull. The holder member 36 enables a surgeon to free his or her hand by attaching the holder member 36 to a patient's skull and/or by placing the support member 10 or a medical or diagnostic device 100 such as a catheter 80 within the holder member 36. The holder member 36 thus engages the support member 10 or the medical or diagnostic device 100.

In one exemplary embodiment, the holder member 36 is formed integrally. In an alternative attunement, the holder member 36 comprises more than two parts which are formed separately and assembled together. At least some parts of the holder member 36 may be malleable so that one or more parts of the holder member 36 may be extended or bent in different directions to accommodate various angles. The holder member 36 thus should be made from a bendable material such as aluminum or a plastic with relief. The material should also be compatible with MRI technology while providing sufficient strength so that the holder member 36 is able to carry the weight of the support member 10, the outer sheath 30, and one or more devices, and/or instruments inserted within the outer sheath 30, and/or one or more additional members of the surgical access system.

In an exemplary configuration, the holder member 36 comprises one or more legs 38 which provide support to the holder member 36, stabilize the holder member 36, and/or allow the holder member 36 to be attached to a surface such as a patient's skull. As is shown in FIG. 2, the legs 38 are shaped to be thin and elongated members. Each leg 38 has one base 40. In one exemplary arrangement, the angle between the base 40 and the leg 38 is adjustable. For example, the bases 40 may be bent to a desired angle to allow for a proper attachment of the holder member 36 to a surface. At least one of the bases 40 may have an opening 42 which serves for attachment of the legs 38 to a curved surface of a patient's skull. For example, the legs 38 may be pinned, screwed, or bolted to the patient's skull. The legs 38 are easy to attach and/or detach so that the holder member 36 may be relocated. In one exemplary arrangement, the legs 38 are flexible and bendable at any desired angle, as was discussed above.

Figure 5:
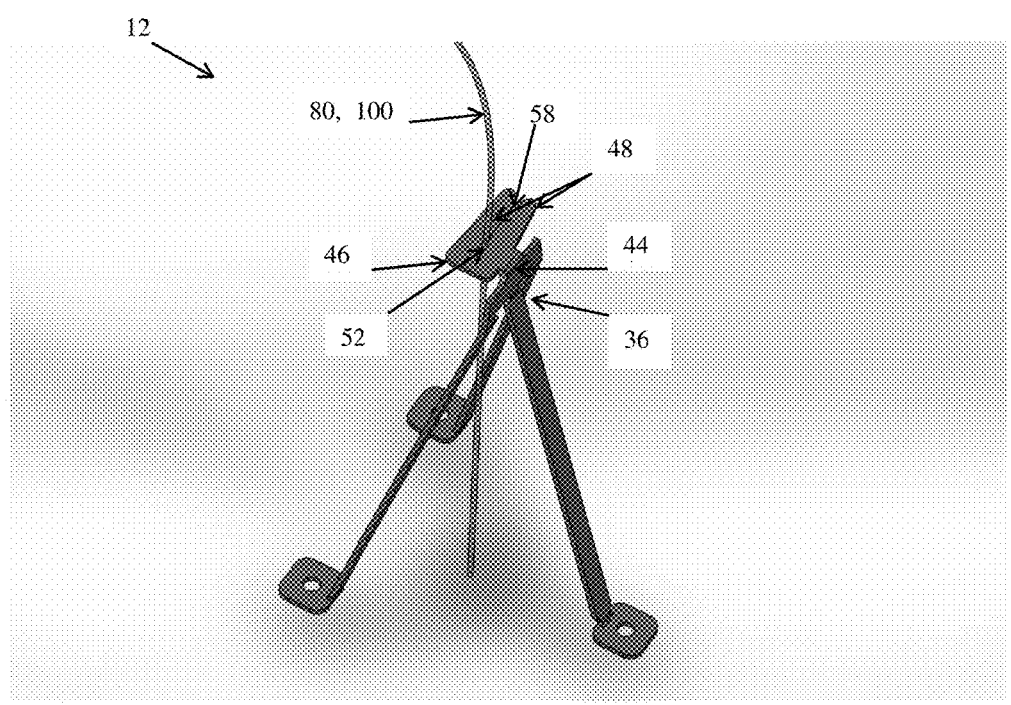
FIG. 5 illustrates an exemplary holder member with a catheter.

In one exemplary arrangement, the legs 38 are spaced apart in a way which provides stability to the holder member 36. For example, as can be seen in FIG. 4, two legs 38 are angled towards the retaining section 18 of the support member 10 while one leg 38 is angled towards the proximal end 16 of the support member 10. The surgeon may manipulate the legs 38 into any desired spacial configuration. The three bases 40, as depicted in FIG. 5 are also bendable to capture a contoured surface and accommodate a curve, for example to allow for attachment to a patient's skull through base openings 42.

In another exemplary configuration, the holder member 36 further comprises a neck portion 44 which connects at least some of the legs 38 with the top portion 46 of the holder member 36. As is shown in FIG. 2, the neck portion 44 is generally thin, yet sturdy enough to carry the weight of the top portion 46 and the support member 10 (as best seen in FIG. 4) or the medical or diagnostic device 100 (as best seen in FIG. 5) inserted into the holder member 36. In one embodiment, the neck portion 44 is bendable to any desired angle.

Referring to FIGS. 2 and 4, the top portion 46 is shown comprising a pair of jaws 48. The jaws 48 run parallel to each other. The jaws 48 run generally perpendicular to the device to be held, such as, for example the support member 10 or a medical or diagnostic device 100 such as a catheter 80, as is illustrated in FIG. 5. Each jaw 48 has an inner edge 54 and an outer 56. The distance between the inner edges 54 of the two jaws 48 defines a channel 58. The inner edges 54 of the pair of jaws 48 terminate in cut outs 50. The cut outs 50 cooperate to define a notch 52. The shape of the notch 52 generally corresponds to the cross section of the engagement portion 32 of the support member 10. As is shown in FIGS. 2 and 4, the notch is shaped as a square. In other exemplary embodiments, the notch may be shaped as a rectangle, an oval, a circle, a diamond, a triangle, a pentagon, a hexagon, an octagon, a trapezoid, the like, or a combination thereof. The jaws 48 have end portions 76. In one exemplary embodiment, the end portions 76 are rounded. The end portions 76 and/or the outer edges 56 of the jaws 48 allow a surgeon to bring the jaws 48 closer together. By doing so, the channel 58 is narrowed and serves as a grip, retaining the device, such as a support member 10 or a catheter 80, secured within the notch 52. The channel 58 thus helps to maintain the position and location of the outer sheath 30 within the support member 10 during imaging and/or during a procedure.

In an alternative embodiment, the proximal section 16 of the support member 10 may include additional stop members (not shown) which may prevent movement of the support member 10 once the support member 10 is engaged in the notch 52 to prevent movement of the support member 10 during diagnosis and/or surgical procedure. The proximal section 16 may further comprise a rotation barrel (not shown) or another member enabling the support member 10 to be selectively rotated about the proximal section 16.

Figure 3:
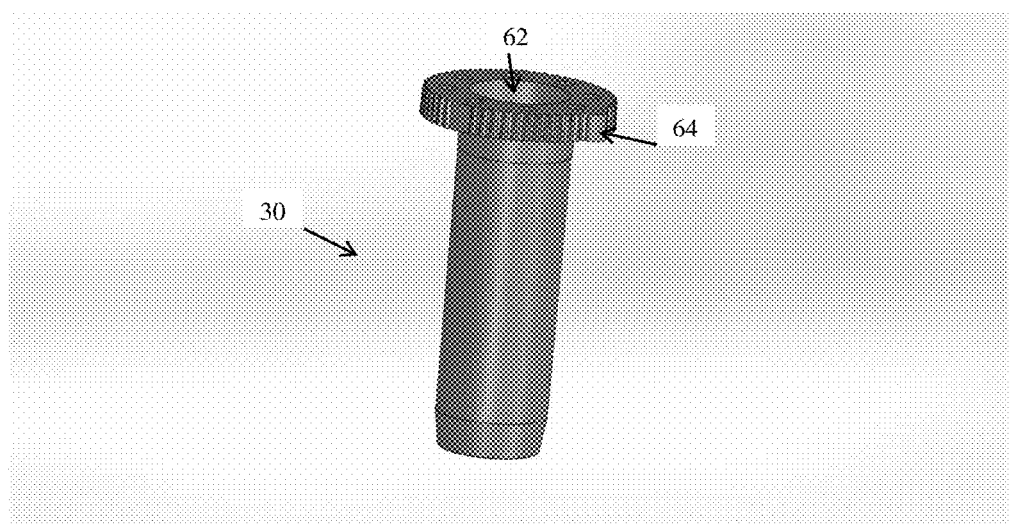
FIG. 3 is an example of an outer sheath of a surgical access system.

FIG. 3 shows an exemplary arrangement of an outer sheath 30 of a surgical access system. An exemplary outer sheath 30 that may be used is described in U.S. Patent Application No. US 2013/0102851, the contents of which are incorporated by reference. In the exemplary arrangement, the outer sheath 30 includes a hollow body 62 and a grip ring 64. The outer sheath 30 may optionally include retaining elements (not shown). As best seen in FIG. 4, the retaining member 26 of the support member 10 engages at least partially around and supports the body 62 of the outer sheath 30. The grip ring 64 or another part of the outer sheath 30 may be secured to the support member 10 temporarily or permanently.

Referring to FIG. 4, a holding arrangement 12 with an outer sheath 30 of a surgical access system supported by a support member 10 is shown. The outer sheath 30 is inserted within the opening 28 of the support member 10. The support member 10 is inserted within the holder member 36 and secured with the pair of jaws 48 of the top portion 46 of the holder member 36. The position of the support member 10 within the holder member 36 may be adjusted, for example, by sliding the engagement portion 32 within the notch 52 of the holder member 36. The entire holding arrangement 12 can be attached and/or secured to a patient's skull through base openings 42.

Referring now to FIG. 5, another exemplary embodiment of a holding arrangement 12 for a surgical access system comprising a holder member 36 and a catheter 80 will be described. As FIG. 5 illustrates, a medical or diagnostic device 100 may be inserted and maintained within the holder member 36. The medical or diagnostic device 100 may be, for example, a catheter 80. The catheter 80 may be inserted through the channel 58 between the pair of jaws 48 and be captured in a notch 52. A surgeon may pinch the pair of jaws 48 together to retain the catheter 80 in place to enable insertion of a catheter 80 into a body cavity for diagnostic or therapeutic purposes, for example to permit injection or withdrawal of fluids or to keep a passage open. At least some parts of the holder member 36 may be bent to allow a surgeon to attach the holder member 36 to patient's skull and/or to retain the catheter 80 in a desired position. As can be seen, the neck portion 44 of the holder member 36 is bent to bring the top portion 46 with the catheter 80 into a horizontal position. The catheter 80 is led horizontally between the legs 38 of the holder member 36.

The method comprises the following steps which may be performed in any order. A surgeon may assemble a holding arrangement 12 (as best seen in FIG. 4) comprising, for example, a support member 10, a holder member 36, and/or outer sheath 30 of a surgical access system with or without an MRI device. The surgeon may utilize an MRI device in conjunction with the holding arrangement 12 during diagnosis and/or surgical procedure. A surgeon may assemble another holding arrangement 12 (as best seen in FIG. 5) comprising a holder member 36 or a medical or diagnostic device 100, such as a catheter 80. A surgeon may hold a support member 10 in his or her hands. Alternatively, the surgeon may free his or her hands by attaching the holder member 36 to a patient's skull, inserting the support member 10 within the notch 52 of the holder member 36, inserting the outer sheath 30 within the opening 28 of the support member 10 or inserting the medical or diagnostic device 100 within the notch 52 of the holder member 36, or a combination thereof. The surgeon may perform at least some of these steps before the outer sheath 30 is inserted into a cranial opening, or afterwards. For example, once the outer sheath 30 is secured by the support member 10, the surgeon may insert the engagement portion 32 of the support member 10 into the notch 52 of the holder member 36. The surgeon may insert the support member 10 within the notch 52 either directly or by leading the support member 10 through the channel 58 to the notch 52. The surgeon may increase the width of the channel 58, for example, by pulling the jaws 48 apart. Once the support member 10 is inserted within the notch 52, the surgeon may adjust the position of the support member 10 by sliding the engagement portion 32 through the notch 52. The surgeon may secure the support member 10 within the notch 52 by narrowing the channel 58, for example, by pinching the outer edges 56 and/or end portions 76 of the pair of jaws 48. Depending on the surgeon's needs such as affording proper balance to the outer sheath and/or one or more devices within the outer sheath, the surgeon may select the length of the engagement portion 32 to insert within the notch 52. The surgeon may do so by laterally positioning the engagement portion 32, for example by sliding the support member back and forth within the notch 52. The surgeon may attach the holder member 36 to a surface, for example a patient's skull, and thus assure that the outer sheath 30 or the medical or diagnostic device 100, such as a catheter 80, is secured and maintained at the desired place, including when the patient is positioned in an MRI bore. The surgeon may attach the holder member 36 utilizing base openings 42 in bases 40 of the legs 38. The surgeon may selectively adjust a position of the holder member 36 by adjusting one or more of the legs 38, one or more bases 40, the pair of jaws 48, the neck portion 44, or a combination thereof. For example, the surgeon may bend the neck portion 44 to bring the top portion 46 of the holder member 36 into a horizontal position.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope and that the method and apparatus within the scope of these claims and their equivalents be covered thereby. In sum, it should be understood that the invention is capable of modification and variation and is limited only by the following claims.

What is claimed is:

1. A holder member of a holding arrangement for a surgical access assembly comprising:
   one or more legs, each leg having a base connected thereto; and
   a pair of jaws,
   wherein the one or more legs, and/or each base of the one or more legs are selectively moveable, wherein the pair of jaws are selectively moveable with respect to each other;
   wherein each jaw within the pair of jaws comprises an inner edge and an outer edge,
   wherein each inner edge comprises a cut out extending inwardly from the inner edge,
   wherein the cut out of each inner edge oppose one another to collectively define a notch; and
   wherein the jaws are generally parallel to each other and define a channel, wherein the channel serves as a stop to retain a support member or a medical or diagnostic device within the notch.

2. The holder member of claim 1, wherein the one or more legs, and each base connected to the one or more legs, or the pair of jaws, are malleable.

3. The holder member of claim 2, wherein each base comprises a base opening for a fastener.

4. The holder member of claim 1, wherein the notch serves as a natural stop to retain a support member or a medical or diagnostic device in place.

5. The holder member of claim 4, wherein the support member or the medical or diagnostic device is compatible with a magnetic resonance imaging device.

6. The holder member of claim 1, further comprising a neck portion that is malleable, wherein the neck portion is positioned between the legs and a top portion that carries the jaws.

7. A holding arrangement for a surgical access assembly comprising:
   a holder member,
   a support member selectively engageable with the holder member,
   wherein at least the support member is compatible with a magnetic resonance imaging device;
   wherein the holder member further comprises:
   one or more legs, each of the one or more legs having a base, a neck portion, and a pair of jaws that are selectively moveable with respect each other, wherein the one or more legs, each base of the one or more legs, the neck portion, and/or the pair of jaws are malleable, and wherein each base is malleable to conform to a non-linear surface and comprises a base opening so that the holder member is attachable to the non-linear surface; and
   wherein the jaws are parallel to each other and define a channel, wherein the channel serves as a stop to retain the support member within a notch that is in communication with the channel.

8. The holding arrangement for the surgical access assembly of claim 7, wherein the support member is configured to support an outer sheath.

9. The holding arrangement of claim 8, wherein the holder member, the support member, the outer sheath, or a combination thereof, are formed from a non-ferrous material.

10. The holding arrangement of claim 9, wherein the holder member, the support member, or both, are formed from a polycarbonate, acrylonitrile butadiene styrene, a blend of polycarbonate and acrylonitrile butadiene styrene, polyolefins, polystyrene, biocompatible resins, aluminum, brass, or other non-ferrous metals, or a combination thereof, and
   the outer sheath is formed from a polycarbonate, acrylonitrile butadiene styrene, a blend of polycarbonate and acrylonitrile butadiene styrene, polyolefins, polystyrene,
   biocompatible resins, or blends thereof.

11. The holding arrangement of claim 8, wherein the support member comprises an engagement portion and the holder member comprises a notch that corresponds with a cross section of the engagement portion, and
   wherein the support member comprises a retaining member, wherein the retaining member is configured to support a body of the outer sheath.

12. The holding arrangement of claim 11, wherein the support member engages the notch of the holder member.

* * * * *